United States Patent [19]

Nagasawa et al.

[11] 3,960,829

[45] June 1, 1976

[54] PROCESS FOR ACYLATION OF AMINO, IMINO AND HYDROXYL GROUPS USING PYRIMIDINE DERIVATIVES

[75] Inventors: Takeshi Nagasawa; Katumasa Kuroiwa; Kouichi Narita, all of Koriyama, Japan

[73] Assignee: Nitto Boseki Co., Ltd., Fukushima, Japan

[22] Filed: Sept. 25, 1974

[21] Appl. No.: 509,221

Related U.S. Application Data

[62] Division of Ser. No. 290,575, Sept. 20, 1972, Pat. No. 3,904,612.

[30] Foreign Application Priority Data

Sept. 22, 1971  Japan ............................... 46-74041
Sept. 23, 1971  Japan ............................... 46-74237
Oct. 19, 1971  Japan ............................... 46-82663

[52] U.S. Cl. ................ 260/112.5 R; 260/239 A; 260/243 R; 260/244 R; 260/247.2 R; 260/247.5 R; 260/250 R; 260/251 QB; 260/269; 260/290 R; 260/302 R; 260/306.7 R; 260/307 R; 260/309; 260/313.1; 260/327 R; 260/333; 260/471 R; 260/479 R; 260/482 R; 260/558 R; 260/558 H; 260/558 S; 260/558 A; 260/561 R; 260/561 A; 260/561 H; 260/561 S; 260/561 HL; 260/562 R; 260/562 H; 260/562 N; 260/562 B; 260/562 P

[51] Int. Cl.² ............... C07C 103/52; C07C 69/00; C07C 125/00

[58] Field of Search ...... 260/112.5, 251 QB, 243 R, 260/244 R, 247.2 R, 247.5 R, 250 R, 269, 290 R, 302 R, 306.7 R, 307 R, 309, 313.1, 327 R, 333, 471 R, 479 R, 482 R, 558 R, 558 H, 561 R, 562 R

[56] References Cited

OTHER PUBLICATIONS

Schroder and Lubke, "The Peptides," vol. 1, Academic Press, New York, 1965, pp. 105–108.
Farrington et al., J. Chem. Soc., 1957, pp. 1407–1413.

*Primary Examiner*—Lewis Gotts
*Assistant Examiner*—Reginald J. Suyat
*Attorney, Agent, or Firm*—Karl W. Flocks

[57] ABSTRACT

Pyrimidine derivatives represented by the formula,

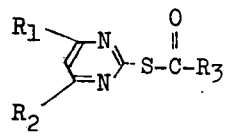

wherein $R_1$ and $R_2$ are individually a hydrogen atom or a methyl group, and $R_3$ is a group formed by removing the carboxyl group from a carboxylic acid, are quite useful in acylating compounds having amino and/or imino and/or hydroxyl groups. The pyrimidine derivatives can easily be prepared by reacting a 2-mercapto-4- and/or 6-methyl-substituted or unsubstituted pyrimidine with a carboxylic acid or a reactive derivative thereof in an inert solvent.

7 Claims, 16 Drawing Figures

PROCESS FOR ACYLATION OF AMINO, IMINO AND HYDROXYL GROUPS USING PYRIMIDINE DERIVATIVES

This is a Division of application Ser. No. 290,575, filed Sept. 20, 1972, now U.S. Pat. No. 3,904,612 of Sept. 9, 1975.

This invention relates to novel pyrimidine derivatives, a process for producing the same and a method for using thereof in acylating amines, hydrazines, alcohols and phenols.

As is well known, peptides are extremely useful compounds for foods and pharmaceuticals or for synthesis of other compounds. A number of peptides have been synthesized and studied heretofore. In the synthesis of peptides there have been used various active esters. The peptide bond, for example, is formed by reacting a N-protected amino acid or N-protected peptide having a free or active carboxyl group with a carboxyl-protected amino acid or carboxyl-protected peptide having a free or active amino group.

In repeated reactions of peptide synthesis, yield is a very important factor. In case the reactions of optically active materials, it is important to maintain the optical activities of the materials without causing racemization during the reactions. Further, it is necessary that after-treatment is easy and pure products can be obtained without causing any side reactions after completion of the reactions.

In order to meet the conditions mentioned above, there have been proposed many carboxylic acid derivatives as active esters. Among these carboxlic acid derivatives, acyl azides are known to have excellent effect on inhibiting racemization. However, the acyl azides have such disadvantages as not only decreasing the yield and easily taking place side reactions but also necessitating much care in storing and handling them and in conducting the reaction under severely controlled conditions since they are unstable.

Other active esters heretofore been proposed have such drawbacks as having selectivity in reaction, that is, they react with only specific amino acids or peptides, resulting in difficulty in purifying the obtained peptides, and the like. Further, there are other drawbacks in the known processes; for example, in acylating various amines, phenols or alcohols wherein they have hydroxyl group together with amino and/or imino groups, when selective acylation of only the amino and/or imino groups is required, as is particularly important in acylating biochemically important saccharides, steroids and the like, the known active esters react not only with the amino and/or imino groups but also with the hydroxyl group, so that the hydroxyl group other than the amino and/or imino groups to be acylated would have previously been protected by other protective groups.

With an aim to overcome the various drawbacks of the known active esters, the present inventors made extensive studies with respect to the funtions and production processes of pyrimidine derivatives to find that the special pyrimidine derivatives are suitable for various useful applications and have markedly excellent functions as acylating agents for acylating amines, hydrazines, alcohols and phenols, above all as active esters in peptide syntheses, and that the pyrimidine derivatives can easily be produced on commercial scale. Based on the above finding, the inventors have accomplished the present invention.

The term "acylation" includes the formation of amide bond, imide bond, ester bond or peptide bond by reacting said pyrimidine derivatives with amines, imines, hydrazines, alcohols, phenols, N-terminal free amino acids or N-terminal free peptides.

The above-mentioned pyrimidine derivatives are novel compounds and processes for acylating amines, hydrazines, alcohols and phenols by use of such novel compounds have not been proposed yet.

An object of the present invention is to provide novel pyrimidine derivatives.

Another object of the present invention is to provide a process for producing the novel pyrimidine derivatives.

A further object of the present invention is to provide a method for using said pyrimidine derivatives as acylating agent or active ester in acylating amines, hydrazines, alcohols and phenols or in peptide syntheses.

Other objects and advantages of the present invention will become apparent from the description made hereinbelow.

The novel pyrimidine derivatives of the present invention are represented by the formula,

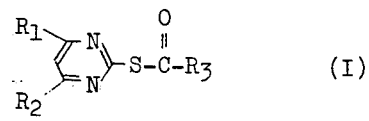

(I)

wherein $R_1$ and $R_2$ are individually a hydrogen atom or a methyl group; and $R_3$ is a group formed by removing the carboxyl group from a carboxylic acid.

The group formed by removing the carboxyl group from a carboxylic acid, represented by $R_3$ in the formula (I), includes those formed by removing the carboxyl group from carboxylic acids such as straight chain or branched chain saturated or unsaturated aliphatic carboxylic acids having 1 to 20 carbon atoms, aromatic carboxylic acids which may contain hetero atoms such as N, S and O, aralkyl caboxylic acids and amino acids wherein the functional groups such as amino group are properly protected. These carboxylic acids mentioned above may contain further various substituents and protected functional groups. Thus $R_3$ includes, for example, an aliphatic radical such as a straight chain or branched chain alkyl group having 1 – 20 carbon atoms, an alkenyl group having 1 – 20 carbon atoms, an alkynyl group having 1 – 20 carbon atoms, an alkoxyalkyl group, a halo- or polyhaloalkyl group; an alicyclic group; an aromatic radical such as a phenyl group, a substituted phenyl group, a tolyl group, a naphthyl group, anthracene; a heterocyclic radical such as a pyridyl group, a furyl group; an aralkyl radical; an protected or non-protected aliphatic amino radical.

The pyrimidine derivatives represented by the formula (I) include, for example, the following compounds:

a. acetyl pyrimidine-2-yl thiolester, acetyl 4-methyl-pyrimidine-2-yl thiolester, acetyl 4,6-dimethyl-pyrimidine-2-yl thiolester, (hereinafter the compounds having 4-methyl and/or 4,6-dimethyl substituents are omitted for simplicity, but they are naturally included in the compounds of the present invention) propionoyl pyrimidine-2-yl thiolester, butyryl pyrimidine-2-yl thiolester, iso-butyryl pyrimidine-2-yl thiolester, crotonoyl pyrimidine-2-yl thiolester, 2,3-dichlorobutyryl pyrimidine-2-yl thiolester, n-valeryl pyrimidine-2-yl thiolester, t-valeryl pyrimidine-2-yl thiolester, caproyl pyrimidine-2-yl thiolester, 5-hydroxylcaproyl pyrimidine-2-yl thiolester, pentenyl-carbonyl pyrimidine-2-yl thiolester {$H_2C=CH.(CH_2)_3.COS-(C_4N_2H_3)$}, octanoyl pyrimidine-2-yl thiolester, dodecanoyl pyrimidine-2-yl thiolester, hexadecanoyl pyrimidine-2-yl thiolester, and the like;

b. benzoyl pyrimidine-2-yl thiolester, p-salicyloyl pyrimidine-2-yl thiolester, p-nitrobenzoyl pyrimidine-2-yl thiolester, p-N,N-dimethylaminobenzoyl pyrimidine-2-yl thiolester, toluoyl pyrimidine-2-yl thiolester, naphthoyl pryrmidine-2-yl thiolester, anthracene-carbonyl pyrimidine-2-yl thiolester, pyridyl-carbonyl pyrimidine-2-yl thiolester, furoyl pyrimidine-2-yl thiolester, and the like;

c. phenylacetyl pyrimidine-2-yl thiolester, p-methoxyphenylacetyl pyrimidine-2-yl thiolester, cinnamoyl pyrimidine-2-yl thiolester, 4-phenylbutyryl pyrimidine-2-yl thiolester, phenylvaleryl pyrimidine-2-yl thiolester, 6-phenylcaproyl pyrimidine-2-yl thiolester, and the like;

d. N-benzyloxycarbonylalanine pyrimidine-2-yl thiolester, (hereinafter the benzyloxycarbonyl group is referred to as "Z"), N-Z-arginine pyrimidine-2-yl thiolester, N-Z-asparagine pyrimidine-2-yl thiolester, N-Z-cystein pyrimidine-2-yl thiolester, N-phthaloyl-glycine pyrimidine-2-yl thiolester, N-Z-histigine pyrimidine-2-yl thiolester, N-tertbutyloxycarbonyl-isoleucine pyrimidine-2-yl thiolester, N-Z-leucine pyrimidine-2-yl thiolester, N-p-methoxybenzyloxycarbonyl-methionine pyrimidine-2-yl thiolester, N-bezhydryloxycarbonyl-phenylalanyl pyrimidine-2-yl thiolester, N-Z-proline pyrimidine-2-yl thiolester, N-Z-serine pyrimidine-2-yl thiolester, N-Z-tyrosine pyrimidine-2-yl thiolester, N-Z valine pyrimidine-2-yl thiolester, and the like.

The pyrimidine derivatives represented by the formula (I) not only can easily be produced on commercial scale from inexpensive industrial reagents, as will be mentioned later, but also are stable and can easily be stored and handled. Moreover, the thiolester portions,

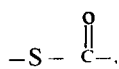

of the compounds of the formula (I) are extremely high in activity, so that these compounds are particularly preferable as acylating agents for compounds having amino and/or imino and/or hydroxyl groups.

In particular, among the compounds represented by the formula (I), the pyrimidine derivatives represented by the formula,

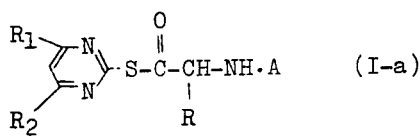

wherein $R_1$ and $R_2$ are as defined in the formula (I); R is the residue group of an amino acid; and A is a protective group for amine, are particularly preferable as acylating agents for N-terminal free amino acids or N-terminal free peptides, that is, as active esters in peptide syntheses.

The pyrimidine derivative represented by the formula (I) is obtained by reacting a 2-mercapto-4- and/or 6-methyl-substituted or unsubstituted pyrimidine represented by the formula (II) with a carboxylic acid or reactive derivative thereof with regard to the carboxyl group in an inert solvent in the presence or absence of a coupling agent, as is clear from the reaction schema shown below.

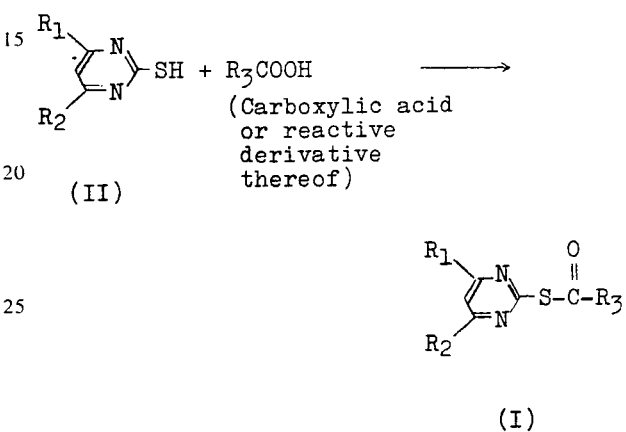

In the above reaction schema, $R_1$, $R_2$, and $R_3$ are as defined in the formula (I).

The compound represented by the formula (II) is a known compound and can easily be obtained according to a known process using an inexpensive industrial reagent. For example, 2-mercapto-pyrimidine can easily be prepared from 1,1,3,3-tetraethoxypropane and thiourea, and 2-mercapto-4,6-dimethyl-pyrimidine can easily be prepared from acetylacetone and thiourea, respectively, in the presence of hydrochloric acid as a catalyst.

Examples of the carboxylic acid or reactive derivative thereof with regard to the carboxyl group include straight chain or branched chain saturated or unsaturated aliphatic carboxylic acids, aromatic carboxylic acids which may contain hetero atoms such as N, S and O, aralkyl carboxylic acids, amino acids wherein the functional groups such as amino group are properly protected, and reactive derivatives of these carboxylic acids with regard to the carboxyl group. The aliphatic carboxylic acids mentioned above may contain straight chain or branched chain saturated or unsaturated alkyl groups having 1 to 20 carbon atoms. Further, the carboxylic acids mentioned above may contain various substituents or properly protected functional groups.

More concretely, the following compounds may be included in the carboxylic acids;

a. aliphatic carboxylic acids: acetic acid, monochloroacetic acid, dichloroacetic acid, trimethylacetic acid, propionic acid, acrylic acid, methacrylic acid, butyric acid, iso-butyric acid, 3-phenylbutyric acid, crotonic acid, 2,3-dichloropropane-1-carboxylic acid, valeric acid, trimethylmethane carboxylic acid, caproic acid, 4-hydroxylpentane-1-carboxylic acid, 6-phenylhexane-1-carboxylic acid, caprylic acid, capric acid, lauric acid, palmitic acid, stearic acid, oleic acid, linoleic acid, and the like;

b. aromatic carboxylic acids: benzoic acid, p-hydroxylbenzoic acid, p-aminobenzoic acid, p-nitrobenzoic acid, p-N,N-dimethylaminobenzoic acid, toluic acid, naphthoic acid, anthracene-1-carboxylic acid, nicotinic acid, furan-3-carboxylic acid, salicyclic acid, and the like;

c. aralkyl carboxylic acids: phenylacetic acid, p-methoxyphenylacetic acid, p-chlorophenylacetic acid, p-ethylphenylacetic acid, p-nitrophenylacetic acid, γ-phenylpropionic acid, 3-phenyl-butyric acid, cinnamic acid, 4-phenyl-n-valeric acid, 5-phenyl-n-caproic acid, and the like;

d. amino acids: α-amino acids of natural occurrence such as alanine (Ala-OH), arginine (Arg-OH), aspartic acid (Asp-OH), asparagine (Asn-OH), cystein (Cys-OH), cystine [(Cys)$_2$], diiodotyrosine [Tyr(I$_2$)], glutamic acid (Glu-OH), glycine (Gly-OH), histidine (His-OH), hydroxyproline (Hyp-OH), isoleucine (Ile-OH), leucine (Leu-OH), lysine (Lys-OH), methionine (Met-OH), norleucine (Nle-OH), ornithine (Orn-OH), phenylalanine (Phe-OH), proline (Pro-OH), serine (Ser-OH), threonine (Thr-OH), tryptophane (Trp-OH), tyrosine (Tyr-OH), valine (Val-OH) and the like; β- and ω-amino acids such as β-alanine, γ-aminobutyric acid, ε-aminocaproic acid and the like; synthetic and semi-synthetic amino acids such as α-methylalanine and the like. (The symbols in the parentheses as well as those appear hereinafter are ordinarily used in the field of peptide chemistry. The protective groups therein are omitted for simplicity, as is the same hereinafter).

In the above-mentioned amino acids, as the protective groups for the functional groups such as amino group, there are, for example, a benzyloxycarbonyl group (Z-), a p-methoxybenzyloxycarbonyl group (pMZ-), a tert-butyroxycarbonyl group (t-BOC-), a tert-amyloxycarbonyl group (t-AOC-), a phthaloyl group (Phth-), a tosyl group (TOS-), a benzhydryloxycarbonyl group (BhOC-) and the like.

As the reactive derivatives of carboxylic acids with regard to the carboxyl group, there may be used all the known reactive derivatives such as acid halides, acid anhydrides, esters, lactones, and acid azides of various carboxylic acids mentioned above. Particularly, acid halides such as acid chlorides and acid bromides; acid anhydrides such as acetic anhydride, propionic anhydride, and benzoic anhydride; and admixed acid anhydrides such as admixed alkylphosphoric anhydrides, admixed alkylcarbonic anhydrides and admixed anhydrides obtained from a carboxylic acid and ethyl chlorocarbonate, are preferably employed.

The reaction between the 2-mercapto-pyrimidine represented by the formula (II) and the carboxylic acid or reactive derivative thereof is carried out in an inert solvent.

When a free carboxylic acid is used in the reaction, it is necessary to add a coupling agent in the reaction system. As the coupling agent, there may be used any known coupling agents, which are usually employed in esterification reaction, such as dicyclohexylcarbodiimide, N,N-diisopropylcarbodiimide, carbonyldiimidazole, N-cyclohexyl-N'-morpholinoethylcarbodiimide and the like.

When a reactive derivative of carboxylic acid is used, it is unnecessary to use a coupling agent.

As the inert solvent used in the above reaction, any solvent is usable so far as it is inert to the reactants and the reaction product and it can dissolve or suspend these reactants or reaction product, and dioxane, ethyl acetate, methylene chloride, chloroform, alkali solution such as aqueous solution of potassium hydroxide and sodium hydroxide, and the like, for example, are preferable.

The reaction temperatures employed therein are not critical, and the reaction may be conducted at such a low temperature as −50°C or such a high temperature as 100°C, or even at the reflux temperature of the solvent employed.

The reaction time depends on the kind of reactants and the reaction temperature employed, and is generally over 30 minutes. In most cases, it is sufficient to react upto 24 hours. But the reaction time as mentioned above is not critical and the reaction may be conducted for less than 30 minutes or over 24 hours.

After completion of the reaction, the reaction solution is purified by a conventional process, for example, by distilling off the solvent followed by recrystallization to obtain the desired pyrimidine derivative represented by the formula (I).

Since the reaction generally proceeds almost quantitatively without accompanying side reactions, the pyrimidine derivative represented by the formula (I) can be obtained extremely high in purity even from unpurified starting materials. Further, the thus obtained pyrimidine derivatives can be used in the form of the reaction solution as it is without being isolated and purified in acylation of amines and the like as hereinafter mentioned in detail to yield highly pure acylated products.

The novel pyrimidine derivatives represented by the formula (I) are quite useful as acylating agents in acylating compounds such as amines, hydrazines, alcohols and phenols, and particularly useful for compounds having hydroxyl groups together with amino and/or imino groups in acylating selectively the amino and/or imino groups therein even though the hydroxyl groups therein are not protected by ordinary protective groups. Further, the pyrimidine derivatives of the present invention are also quite useful as acylating agents, i.e. active esters in peptide syntheses, since they react with N-terminal free amino acids having protected carboxyl groups to obtain compounds having peptide bonds in high yield without racemization and side reactions under certain conditions with extremely faster reaction rate than the known active esters such as carboxylic acid derivatives.

In the next place, a process for acylating, including peptide synthesis, various amines, hydrazines, phenols and alcohols by using as acylating agents the pyrimidine derivatives represented by the formula (I) is explained below.

The acylation of a compound having amino and/or imino and/or hydroxyl groups or a salt thereof comprises reacting said compound with the pyrimidine derivative of the formula (I) in an inert solvent in the presence or absence of a base, as shown by the following reaction schema:

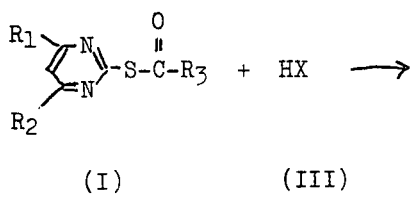

(I)          (III)

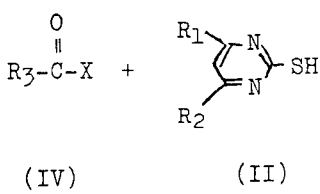

(IV)        (II)

In the above schema, $R_1$, $R_2$ and $R_3$ are as defined in the formula (I); and H in the formula (III) is a hydrogen atom in the amino or imino or hydroxyl group; and X is a residual group of the compound formed by removing one hydrogen atom from the amino or imino or hydroxyl group thereof.

The compounds represented by the formula (III) include univalent amines, imines, alcohols or phenols, or those having two or more amino and/or imino groups, or those having two or more hydroxyl groups, and further they may be compounds having both one or more amino and/or imino groups and one or more hydroxyl groups. When the compound of the formula (III) has plural functional groups and all of the functional groups are to be acylated, the pyrimidine derivative of the formula (I) is used in an amount corresponding to the numbers of the functional groups. The hydroxyl group mentioned above means both alcoholic and phenolic hydroxyl groups.

Examples of the compound having amino and/or imino and/or hydroxyl groups represented by the formula (III) include a wide scope of compounds such as aliphatic, alicyclic, aralkyl, aromatic and heterocyclic primary and secondary amines; hydrazines and derivatives thereof; N-terminal free amino acids or peptides having protectd carboxyl groups; various saccharides and steroids having amino and/or imino and/or hydroxyl groups; aliphatic, alicyclic, aralkyl, aromatic and heterocyclic alcohols and phenols; and various aliphatic, alicyclic, aralkyl, aromatic and heterocyclic compounds having both amino and/or imino groups and hydroxyl groups. The compound represented by the formula (III) may contain one or more other various substituent groups or protected functional groups.

Examples of such compounds are as shown below.

A. Methylamine, dimethylamine, ethylamine, ethylenediamine, diethylenetriamine, ethanolamine, isopropylamine, butylamine, t-butylamine, N-ethyl-N-$\beta$-hydroxyethylamine, octylamine, laurylamine, and the like.

B. Cyclohexylamine and the like.

C. Benzylamine, p-chlorobenzylamine, p-methoxybenzylamine, p-nitrobenzylamine, 3-phenylpropylamine, 3-(p-methoxyphenyl)-propylamine, and the like.

D. Aniline, N-methylaniline, p-methylaniline, p-aminophenol, p-methylaminophenol, toluidine, xylidine, o-carbomethylaniline; p-phenetidine, diphenylamine, $\alpha$-(or $\beta$-)naphthylamine, 4-aminonaphthol, and the like.

E. Ethyleneimine, pyrrolydine, pryazole, indole, and the like.

F. Hydrazine, phenylhydrazine, 2,4-dinitrophenylhydrazine, N-methyl-N-phenylhydrazine, and the like.

G. Amino acids of natural ocurrence having free amino and/or imino groups and protected carboxyl groups and synthetic and semi-synthetic amino acids: $\alpha$-amino acids of natural occurrence such as Ala-OH, Arg-OH, Asp-OH, Asn-OH, Cys-OH, Glu-OH, Gly-OH, His-OH, Hyp-OH, Ile-OH, Leu-OH, Lys-OH, Met-OH, Nle-OH, Orn-OH, Phe-OH, Pro-OH, Ser-OH, Thr-OH, Trp-OH, Tyr-OH, Val-OH and the like; $\beta$- and $\omega$-amino acids such as $\beta$-alanine, $\gamma$-aminobutyric acid, $\epsilon$-aminocaproic acid and the like; synthetic and semi-synthetic amino acids such as $\alpha$-methylalanine and the like; peptides obtained by coupling reaction of two or more amino acids. (The protective groups therein are omitted for simplicity, as is the same hereinafter.)

The carboxyl groups in these amino acids and peptides may be protected by alkyl esters such as methyl ester, ethyl ester, and the like, or salts such as sodium salt, potassium salt, magnesium salt and the like, or acid amides, as is the same as in known processes for synthesizing peptides. After completion of the reaction, these protective groups for the carboxyl groups or those derived from the compound of the formula (I), e.g., protective groups for amine, can be removed by a known process, if necessary.

H. Saccharides and steroids such as 2-amino-1,6-anhydro-2-deoxy-$\beta$-D-glucopyranose, L-glucosamine, methyl-3-amino-$\beta$-L-xylopyranoside, and the like.

J. Methyl alcohol, ethyl alcohol, isopropyl alcohol, amyl alcohol, octyl alcohol, lauryl alcohol, phenol, cathechol, naphthol, benzyl alcohol, cyclohexanol, and the like.

In the compounds represented by the formula (III), the compound having amino and/or imino groups may be subjected to acylation reaction in the form of a free amine or imine or a salt thereof such as, for example, hydrochloride, hydrobromide, hydroiodide, sulfate, sulfite or the like. In case the compound is subjected to the reaction in the form of a salt, it is necessary to add a base as a deacidifying agent to the reaction system. As the deacidifying agent, there may be used any conventional deacidifying agents, for example, organic tertiary amines such as triethylamine, N-alkylmorpholine, N,N-dialkylaniline, pyridine, xynoline and the like or inorganic bases such as a hydroxide, carbonate or bicarbonate of alkali metal, for example, potassium hydroxide, sodium hydroxide, potassium carbonate, sodium carbonate, potassium bicarbonate, sodium bicarbonate and the like.

The reaction between the compound of the formula (I) and the compound of the formula (III) is carried out in an inert solvent.

As the inert solvent, any solvents which are inert to the reactants and the reaction product may be used. Examples of the inert solvent include dioxane or aqueous solution thereof, chloroform, methylene chloride, ethyl acetate and the like. When dioxane or ethyl acetate is used as the solvent, liberated pyrimidine of the formula (II) in the coupling reaction is precipitated.

The above-mentioned reaction may generally be carried out at a temperature between −50 and 100°C. In case the reaction is carried out below about −20°C, the acylation of the hydroxyl group is inhibited substantially 100 %. Therefore, the esterification reaction according to present acylation reaction must be carried out at least about −20°C or higher. Generally the esterification reaction is carried out at room temperature or higher. When selective acylation of the amino and/or imino groups is required to the compound having both the hydroxyl group and amino and/or imino groups, the reaction is preferably carried out below −20°C, since the acylation of the hydroxyl group does not substantially take place below −20°C. In acylating saccharides or steroids having both hydroxyl groups and amino and/or imino groups, and selective acylation of the amino and/or imino groups being required, it is necessary to protect the hydroxyl groups by protective groups such as a benzyl group, a carbobenzoxy group and the like according to known processes. On the contrary, in the present process it is not necessary to protect the hydroxyl group by any protective group, since selective acylation of the amino and/or imino groups therein is possible below about −20°C.

In case the pyrimidine derivative of the formula (I-a) is used as a reactive ester in peptide synthesis, e.g. the coupling reaction of the compound of the formula (I-a) and N-terminal free amino acid or peptide, it is preferable to carry out the reaction at a temperatre between −50 and 6°C. But the acylation temperatures mentioned above are not critical.

In the acylation reaction mentioned above, the reaction is completed in most case within 30 minutes, or within 6 hours at the longest. According to the present process, the reaction proceeds with extremely great reaction rate even at a low temperature. However, the acylation of phenols or alcohols takes relatively longer reaction time and the yield thereof is also relatively low when compared with the reaction of amines. In the above case, there may be used a known catalyst for esterification such as acetic acid, 2-hydroxypyridine and the like.

In the acylation reaction using the pyrimidine derivative of the formula (I), there are many advantages as mentioned below:

Compounds having amino and/or imino and/or hydroxyl groups are easily acylated under mild conditions to yield the corresponding amides (or imides), peptides or esters in high yield.

The pyrimidine derivatives of the formula (I) have little selectivity to the reactants and easily react with any amines (or imines), hydrazines, alcohols or phenols.

Contrary to the known active esters which have mostly selectivity to N-terminal free amino acids or peptides in the coupling reaction therewith, the pyrimidine derivatives of the formula (I) do not show such selectivity and easily react with any amino acids or peptides.

In the acylation of the compounds having amino and/or imino and/or hydroxyl groups with other active groups such as carboxyl or imidazole, the pyrimidine derivatives of the formula (I) can react preferentially and selectively with the amino and/or imino and/or hydroxyl groups, which cannot be expected in the known acylating agents.

In the acylation of the compounds having both amino and/or imino groups and hydroxyl groups using the pyrimidine derivatives of the formula (I), the amino and/or imino groups therein can selectively be acylated without protecting the hydroxyl groups therein by conducting the reaction below about −20°C.

According to the acylation reaction using the pyrimidine derivatives of the formula (I), the purification of the acylated products is extremely easy.

In the acylation reaction using the pyrimidine derivatives of the formula (I), 2-mercapto-pyrimidine or a derivative thereof represented by the formula (II) is produced with the proceeding of the reaction and is liberated and is sometimes precipitated from the reaction solution containing the acylated product. Thus the separation of said 2-mecapto-pyrimidine of the formula (II) is easy and further the remaining rate of said 2-mercapto-pyrimidine in the reaction solution containing the acylated product is very low. Further, since the 2-mercapto-pyrimidine of the formula (II) is an amphoteric compound and is easily dissolved in both an acid and an alkali, even though it is retained in the reaction solution containing the acylated product, it can easily be removed by washing the reaction solution with a dilute acid or dilute alkali aqueous solution. Thus the acylated product can be obtained in extremely high purity. In case the 2-mercapto-pyrimidine of the formula (II) is dissolved in the solvent, it can easily be removed by washing the reaction solution with a dilute acid or dilute alkali aqueous solution using the same procedure as mentioned above.

Although purification of the produced peptide is most important problem in peptide synthesis, the produced peptide can be obtained in high purity and in high yield according to the process using the pyrimidine derivative of the formula (I) as an active ester, since the produced 2-mercapto-pyrimidine of the formula (II) can easily be removed as mentioned above.

In the peptide synthesis of optically active materials, it is important to conduct the reaction with maintaining the optical activities of the materials without causing racemization. According to the process using the pyrimidine derivative of the formula (I) as an active ester, a peptide bond can easily be formed with extremely greater reaction rate than that using other known active ester without causing racemization or without accompanying side reactions under certain reaction conditions such as mild conditions, for example, conducting the reaction under relatively low temperature.

The accompanying drawings are the infrared spectra of the pyrimidine derivatives represented by the formula (I) (FIG. 1 – FIG. 7) and those of the acylated products according to the processes of Examples mentioned hereinbelow (FIG. 8 – FIG. 16).

Procedures for preparing 2-mercapto-4 - and/or 6-methyl-substituted or unsubstituted pyrimidines which are starting materials for production of the pyrimidine derivatives represented by the formula (I) are explained below with reference to referential examples.

REFERENTIAL EXAMPLE 1

Synthesis of 2-mercapto-pyrimidine

A solution of 61 g (0.80 mole) of thiourea in 600 ml of ethanol was charged into a 2-liter three-necked flask equipped with a stirrer and a reflux condenser, and 200 ml of concentrated hydrochloric acid was added to the solution, whereby the liquid became homogenous after several minutes. This liquid was mixed with 176 g (0.80 mole) of 1,1,3,3-tetraethoxypropane, and the resulting mixture was reacted under reflux for about 1 hour. After completion of the reaction, the reaction liquid was cooled to 10°C in an ice bath and maintained at said temperature for 30 minutes to deposit 2-mercapto-pyrimidine hydrochloride in the form of yellow crystals. The crystals were collected in a Buchner funnel, washed with 100 ml of cold alcohol and then dried at room temperature to obtain 89 g of crude 2-mercapto-pyrimidine hydrochloride in yield of 75 %.

The crude 2-mercapto-pyrimidine hydrochloride (25 g, 0.17 mole) was suspended in 50 ml of water, and the resulting suspension was adjusted to pH 7 to 8 by addition of 27 ml of a 20 % aqueous solution hydroxide solution, whereby 2-mercapto-pyrimidine was precipitated. This 2-mercapto-pyrimidine was recovered by filtration with a Buchner funnel, washed with 50 ml of cold water and then recrystallized from a solution comprising 300 ml of water and 300 ml of ethanol to obtain 19 g of 2-mercapto-pyrimidine in yield of 70 %.

Elementary analysis:

|  | C(%) | H(%) | N(%) | S(%) |
|---|---|---|---|---|
| Calcd. for $C_4H_4N_2S$ | 42.84 | 3.59 | 24.98 | 28.59 |
| Found | 42.91 | 3.68 | 24.92 | 28.48 |

REFERENTIAL EXAMPLE 2

Synthesis of 2-mercapto-4,6-dimethyl-pyrimidine

Thiourea (76 g, 1.0 mole) was suspended in a solution of 120 g (1.2 moles) of acetylacetone in 2,500 ml of ethanol. The resulting suspension was mixed with 250 ml of concentrated hydrochloric acid, and then reacted under reflux for 2 hours. After completion of the reaction, the reaction liquid was cooled, whereby beautiful yellow needle-like crystals of 2-mercapto-4,6-dimethyl-pyrimidine hydrochloride were formed. The reaction liquid was allowed to stand for a day to deposit sufficiently the crystals, which were then recovered by filtration and dried to obtain 140 g of 2-mercapto-4,6-dimethyl-pyrimidine hydrochloride in yield of 80 %.

To the filtrate after recover of the above-mentioned pyrimidine hydrochloride were again added 110 g of acetylacetone, 76 g of thiourea, 100 ml of ethanol and 150 ml of concentrated hydrochloric acid, and the resulting mixture was subjected to filtration and drying to obtain 158 g of 2-mercapto-4,6-dimethyl-pyrimidine hydrochloride in yield of 90 %. The filtrate in this case was again subjected to the same operation as above to obtain 148 g of 2-mercapto-4,6-dimethyl-pyrimidine hydrochloride in yield of 84 %.

The above-mentioned 2-mercapto-4,6-dimethyl-pyrimidine hydrochloride (200 g, 1.13 moles) was suspended in 400 ml of water, and the resulting suspension was heated to about 40°C, while gradually adding thereto 70 ml of a 20 % aqueous sodium hydroxide solution, whereby the 2-mercapto-4,6-dimethyl-pyrimidine hydrochloride was completely dissolved. This solution was adjusted to pH 4.5 to 5.0 by gradual addition of a 20 % aqueous sodium hydroxide solution, whereby pale yellow crystals of 2-mercapto-4,6-dimethyl-pyrimidine were precipitated. The reaction liquid was allowed to stand for a day at room temperature to sufficiently deposit the crystals, which were then recovered by filtration and dried to obtain 117 g of 2-mercapto-4,6-dimethyl-pyrimidine in yield of 74.3 %.

Elementary analysis:

|  | C(%) | H(%) | N(%) | S(%) |
|---|---|---|---|---|
| Calcd. for $C_6H_8N_2S$ | 51.40 | 5.75 | 19.98 | 22.87 |
| Found | 51.52 | 5.75 | 20.03 | 22.75 |

Procedures for producing the present pyrimidine derivatives represented by the formula (I) are illustrated below with reference to examples.

Examples 1 to 9 relate to processes for preparing acyl 4- and/or 6-methyl-substituted or unsubstituted pyrimidine-2-yl thiolesters.

EXAMPLE 1

Synthesis of acetyl pyrimidine-2-yl thiolester

2-Mercapto-pyrimidine (2.24 g, 0.02 mole) was suspended in 20 ml of dioxane, and 10.2 g (0.10 mole) of acetic anhydride was dropped into the resulting mixture at room temperature and reacted. After 20 hours the solution became completely transparent and the reaction was completed. Then the solvent and the excess acetic anhydride were distilled off under reduced pressure from the reaction solution. The residue was recrystallized from an benzene-petroleum ether solvent to obtain 2.20 g of acetyl pyrimidine-2-yl thiolester; yield, 72 %; m.p. 58°C.

Elementary analysis:

|  | C(%) | H(%) | N(%) | S(%) |
|---|---|---|---|---|
| Calcd. for $C_6H_6ON_2S$ | 46.74 | 3.92 | 18.17 | 20.79 |
| Found | 46.88 | 4.08 | 18.23 | 20.87 |

FIG. 1 shows the infrared spectrum of acetyl pyrimidine-2-yl thiolester. The infrared spectrum shows the presence of

in the thiolester bond (1700 cm$^{-1}$) and the pyrimidine ring (1550 and 1383 cm$^{-1}$).

EXAMPLE 2

Synthesis of acetyl 4,6-dimethyl-pyrimidine-2-yl thiolester

Using a similar procedure to Example 1, 2-mercapto-4,6-dimethyl-pyrimidine was reacted with acetic anhydride. After distilling off the solvent and recrystallization, 16.6 g of acetyl 4,6-dimethyl-pyrimidine-2-yl thiolester having a melting point of 19.5 - 21.0°C was obtained in yield of 91 %.

Elementary analysis:

|  | C(%) | H(%) | N(%) | S(%) |
|---|---|---|---|---|
| Calcd. for $C_8H_{10}ON_2S$ | 52.73 | 5.53 | 15.37 | 17.59 |
| Found | 52.59 | 5.43 | 15.36 | 17.54 |

FIG. 2 shows the infrared spectrum of acetyl 4,6-dimethyl-pyrimidine-2-yl thiolester. The infrared spectrum shows the presence of

in the thiolester bond (1708 cm$^{-1}$) and the pyrimidine ring (1585 and 1260 cm$^{-1}$).

EXAMPLE 3

Synthesis of benzoyl pyrimidine-2-yl thiolester

After dissolving 11.2 g (0.10 mole) of 2-mercapto-pyrimidine in a solution of 20 ml of water containing 6.6 g of potassium hydroxide, 15.4 g (0.11 mole) of benzoyl chloride in 40 ml of ethyl acetate was dropped with stirring into the resulting mixture under ice cooling, and reacted. After allowing the reaction solution to stand for a day at room temperature, it was washed three times with an aqueous saturated sodium bicarbonate solution, twice with a 2N aqueous hydrochloride acid solution and twice with a 10 % aqueous sodium chloride solution. The ethyl acetate layer was dried over anhydrous sodium sulfate and the ethyl acetate was distilled off. The residue was recrystallized from ether to obtain 14.1 g of benzoyl pyrimidine-2-yl thiolester; yield, 65 %; m.p. 54°–55°C.

Elementary analysis:

|  | C(%) | H(%) | N(%) | S(%) |
|---|---|---|---|---|
| Calcd. for $C_{11}H_8ON_2S$ | 61.09 | 3.73 | 12.95 | 14.83 |
| Found | 61.13 | 3.84 | 12.76 | 14.85 |

FIG. 3 shows the infrared spectrum of benzoyl pyrimidine-2-yl thiolester. The infrared spectrum shows the presence of

in the thiolester bond (1673 cm$^{-1}$) and the pyrimidine ring (1552 and 1382 cm$^{-1}$).

EXAMPLE 4

Synthesis of benzoyl 4,6-dimethyl-pyrimidine-2-yl thiolester

Using a similar procedure to Example 3, 2-mercapto-4,6-dimethyl-pyrimidine was reacted with benzoyl chloride. After washing, distilling off the solvent and recrystallization, there was obtained 17.8 g of benzoyl 4,6-dimethyl-pyrimidine-2-yl thiolester; yield, 73 %; m.p. 76°–77°C.

Elementary analysis:

|  | C(%) | H(%) | N(%) | S(%) |
|---|---|---|---|---|
| Calcd. for $C_{13}H_{12}ON_2S$ | 63.91 | 4.95 | 11.47 | 13.12 |
| Found | 63.89 | 4.90 | 11.39 | 13.12 |

FIG. 4 shows the infrared spectrum of benzoyl 4,6-dimethyl-pyrimidine-2-yl thiolester. The infrared spectrum shows the presence of

in the thiolester bond (1684 cm$^{-1}$) and the pyrimidine ring (1584 and 1254 cm$^{-1}$).

EXAMPLE 5

Synthesis of cinnamoyl pyrimidine-2-yl thiolester

After dissolving 11.2 g (0.10 mole) of 2-mercapto-pyrimidine in a solution of 6.6 g of potassium hydroxide in 20 ml of water, 26.7 g (0.11 mole) of cinnamoyl chloride in 40 ml of ethyl acetate was dropped with stirring into the resulting mixture under ice cooling and reacted at room temperature for a day. After completion of the reaction, usin a similar procedure of washing, distilling off the solvent and recrystallization to Example 3, 17.1 g of cinnamoyl pyrimidine-2-yl thiolester having a melting point of 86°–87°C was obtained in yield of 76 %.

Elementary analysis:

|  | C(%) | H(%) | N(%) | S(%) |
|---|---|---|---|---|
| Calcd. for $C_{13}H_{10}ON_2S$ | 64.44 | 4.16 | 11.56 | 13.23 |
| Found | 64.52 | 4.32 | 11.39 | 13.34 |

FIG. 5 shows the infrared spectrum of cinnamoyl pyrimidine-2-yl thiolester. The infrared spectrum shows the presence of

in the thiolester bond (1659 cm$^{-1}$) and the pyrimidine ring (1550 and 1385 cm$^{-1}$).

EXAMPLE 6

Synthesis of N-benzyloxycarbonyl-glycine pyrimidine-2-yl thiolester

2-Mercapto-pyrimidine (1.12 g, 0.01 mole) was suspended in 50 ml of ethyl acetate, and 2.21 g (0.01 mole) of N-benzyloxycarbonylglycine was added to the resulting suspension and successively 2.06 g (0.01 mole) of dicyclohexylcarbodiimide was added thereto with stirring at 0°C and reacted. Within 5 minutes dicyclohexylurea began to precipitate and deposit, and 2-mercapto-pyrimidine was consumed completely in about 4 hours. After allowing the reaction solution to stand overnight at 0°C, the precipitate of dicyclohexylurea was filtered off and the filtrate was washed twice with 30 ml of an aqueous saturated sodium chloride solution and dried over anhydrous sodium sulfate followed by distilling off ethyl acetate under reduced pressure at room temperature to yield oily substance. The oily substance was dissolved in a small amount of a ethyl acetate ether solvent and allowed to stand to obtain pale yellow crystals of N-benzyloxycarbonyl-glycine-pyrimidine-2-yl thiolester; yield, 88 % (2.67 g); m.p. 130°–131°C.

Elementary analysis:

|  | C(%) | H(%) | N(%) | S(%) |
|---|---|---|---|---|
| Calcd. for $C_{14}H_{13}O_3N_3S$ | 55.43 | 4.31 | 13.85 | 10.57 |
| Found | 55.38 | 4.26 | 13.70 | 10.35 |

EXAMPLE 7

Synthesis of N-benzyloxycarbonyl-glycine pyrimidine-2-yl thiolester

After 0.02 mole of 2-mercapto-pyrimidine was dissolved in 80 ml of methylene chloride, 0.02 mole of N-benzyloxycarbonyl-glycine was added to the resulting solution, and then 0.02 mole of dicyclohexylcarbodiimide was added thereto under ice cooling and reacted for 3 hours. After cooling the reaction solution sufficiently, the produced precipitate of dicyclohexylurea was filtered off. The methylene chloride in the filtrate was distilled off under reduced pressure at room temperature and the residue was recrystallized from a ethyl acetate-petroleum ether solvent. The obtained pale yellow crystals have a melting point of 130°–131°C, which was identified as the same compound as obtained in Example 6 from the results of elementary analysis. The yield of it was 90 %.

EXAMPLE 8

2-Mercapto-4,6-dimethyl-pyrimidine (0.01 mole) was suspended in 50 ml of ethyl acetate and 0.01 mole of N-benzyloxycarbonylamino N-benzyloxycarbonyl-amino as listed in Table 1 was added to the resulting suspension, and then 0.01 mole of dicyclohexylcarbodiimide was added under ice cooling and reacted for 2 hours. After completion of the reaction, the dicyclohexylurea was filtered and the ethyl acetate in the filtrate was distilled off under reduced pressure at 30°C. The residue was recrystallized from an ethyl acetate-petroleum ether solvent to obtain the corresponding N-benzyloxycarbonyl-amino acid 4,6-dimethyl-pyrimidine-2-yl thiolester. Table 1 shows the obtained resuts.

FIG. 6 shows the presence of —NH— (3220 cm⁻¹),

in the ester bond (1714 cm⁻¹), the pyrimidine ring (1587 and 1522 cm⁻¹) and

(1248 cm⁻¹).

Figure 1:
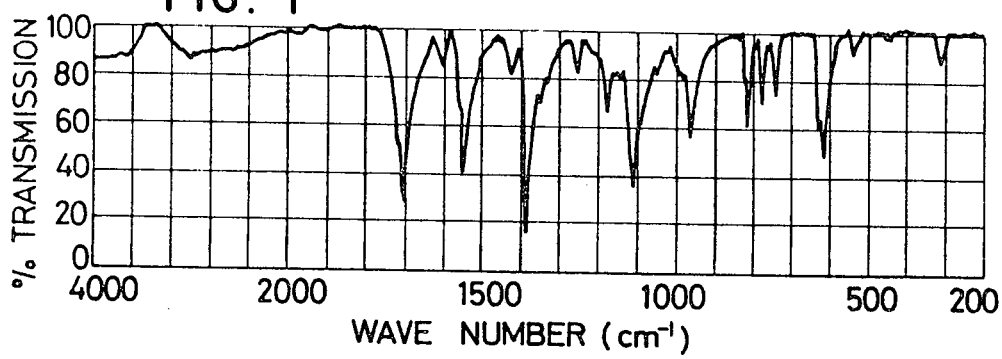
Figure 2:
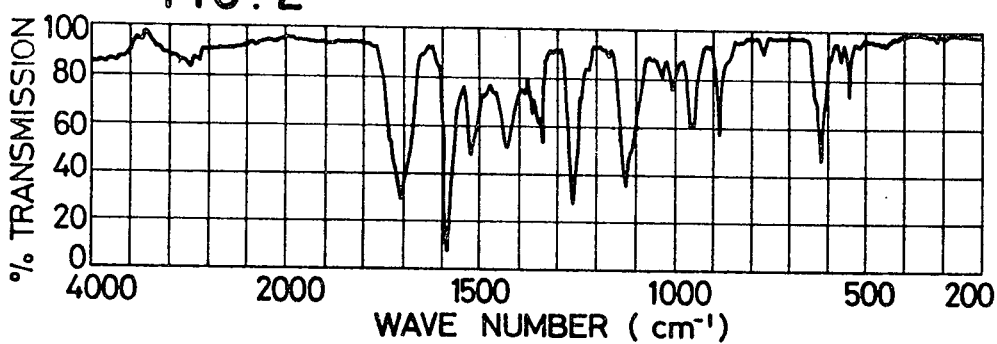
Figure 3:
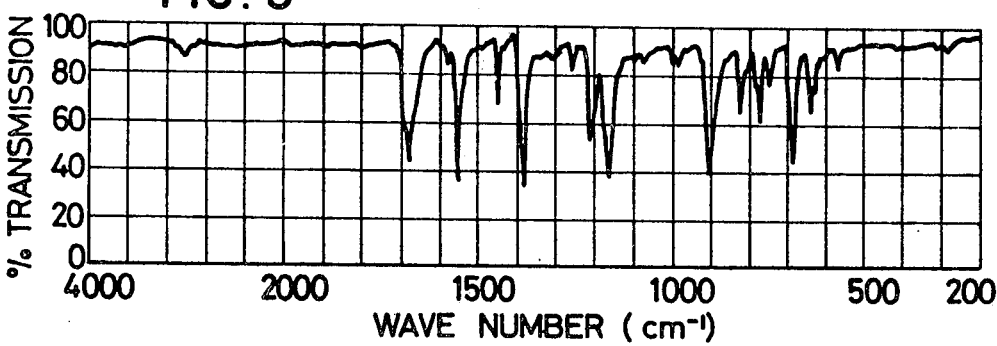
Figure 4:
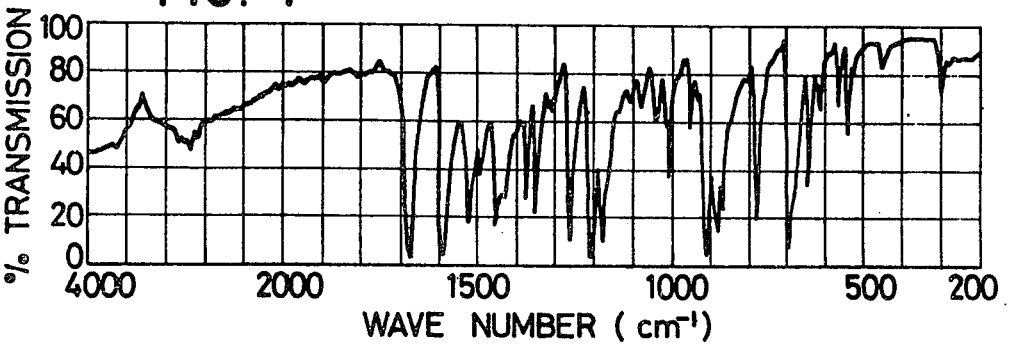
Figure 5:
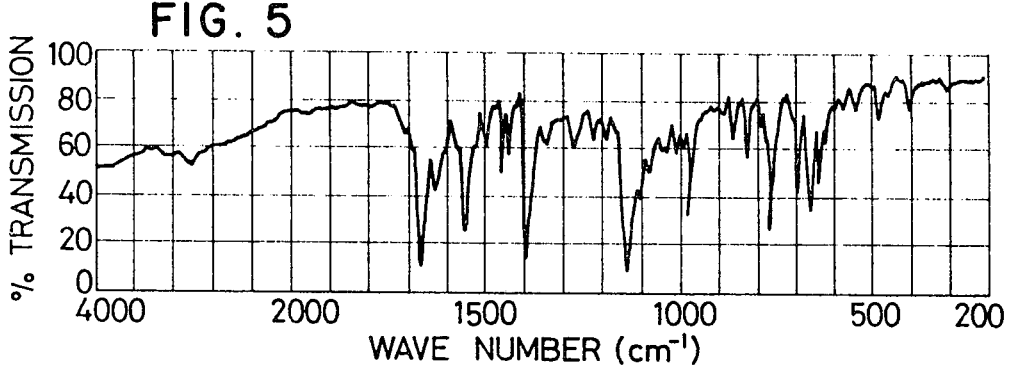
Figure 6:
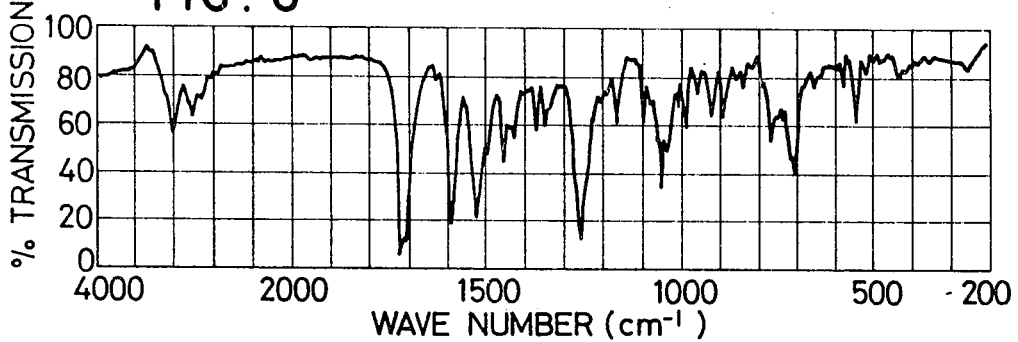
FIG. 6 and FIG. 7 show the infrared spectra of the resulting compounds of Run Nos. 2 and 3 in Table 1.
Figure 7:
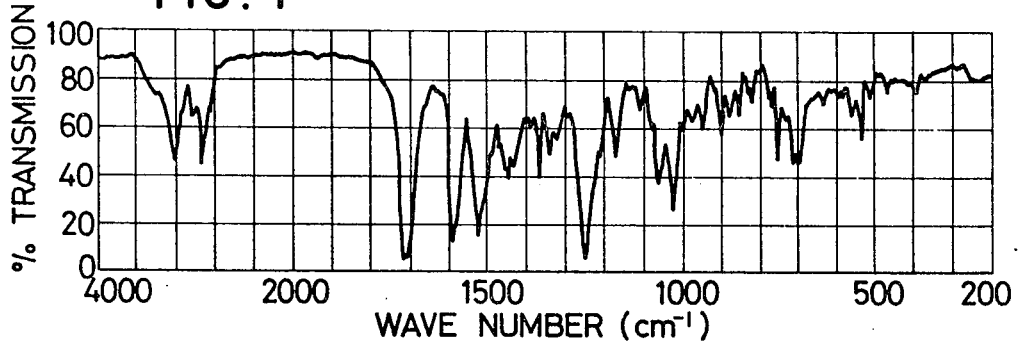

FIG. 7 shows the presence of —NH— (3220 cm⁻¹),

in the ester bond (1705 cm⁻¹), the pyrimidine ring (1587 and 1520 cm⁻¹) and

(1244 cm⁻¹).

Table 1

| Run No | Z-amino acid | N-Z-amino acid 4,6-dimethyl-pyrimidine-2-yl thiolester | Yield (%) | M.P. (°C) | | Elementary analysis (%) C | H | N | S |
|---|---|---|---|---|---|---|---|---|---|
| 1 | Z-L-Ala-OH | Z-L-Ala-S-(4,6-dimethylpyrimidin-2-yl) | 85 | 110 – 111 | Calcd. | 59.11 | 5.54 | 12.16 | 9.28 |
| | | | | | Found | 59.25 | 5.63 | 12.23 | 9.18 |
| 2 | Z-L-Phe-OH | Z-L-Phe-S-(4,6-dimethylpyrimidin-2-yl) | 92 | 139 – 140 | Calcd. | 65.50 | 5.50 | 9.97 | 7.61 |
| | | | | | Found | 65.70 | 5.65 | 9.87 | 7.70 |
| 3 | Z-L-Leu-OH | Z-L-Leu-S-(4,6-dimethylpyrimidin-2-yl) | 83 | 113.0 – 113.5 | Calcd. | 61.99 | 6.50 | 10.86 | 8.27 |
| | | | | | Found | 62.08 | 6.47 | 10.76 | 8.28 |
| 4 | Z-DL-Ala-OH | Z-DL-Ala-S-(4,6-dimethylpyrimidin-2-yl) | 87 | 104 – 105 | Calcd. | 59.11 | 5.54 | 12.16 | 9.28 |
| | | | | | Found | 59.40 | 5.67 | 12.12 | 9.26 |

1) Z: a benzyloxycarbonyl group ( 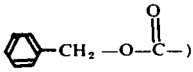 )

EXAMPLE 9

Synthesis of N-benzyloxycarbonyl-L-alanine 4,6-dimethyl-pyrimidine-2-yl thiolester N-benzyloxycarbonyl-L-alanine (0.05 mole) and 0.05 mole of triethylamine were dissolved in 100 ml. of methylene chloride, and 0.05 mole of ethyl chlorocarbonate was dropped in the resulting solution under cooling at —5°C. After 15 minutes, a solution of 0.06 mole of 2-mercapto-4,6-dimethyl-pyrimidine in 50 ml of methylene chloride was added to the resulting solution and reacted for 2 hours. The thus obtained reaction solution was washed with water and then the solvent was distilled off under reduced pressure to obtain pale yellow oily substance. When said substance was recrystallized from an ethyl acetate-petroleum ether solvent, the obtained crystals showed a melting point of 110°–111°C. The data of elementary analysis showed that the obtained crystals were the same compound as that obtained in Example 8, Run No. 1. The yield thereof was 85 %.

The following Examples 10 to 13 relate to the acylation of amines, hydrazines, alcohols and phenols using the pyrimidine derivatives represented by the formula (I).

EXAMPLE 10

The pyrimidine derivative of the formula (I), which has been obtained from the procedure of Example 1, 3 or 5, as listed in Table 2, (0.01 mole) was dissolved in 20 ml of ethyl acetate. After cooling the resulting solution to 0°C, 0.01 mole of the amine or hydrazine as listed in Table 2 was added thereto and successively 10 ml of ethyl acetate was added. The reaction was carried out at 20°–25°C for 30 minutes. The reaction was initiated within a very short time (within about 5 minutes) and 2-mercapto-pyrimidine was deposited with the progress of the reaction. After completion of the reaction, the 2-mercapto-pyrimidine was filtered off and the filtrate was washed with an aqueous saturated sodium bicarbonate solution, and aqueous saturated sodium chloride solution, a 0.5 N aqeuous hydrochloric acid solution and an aqueous saturated sodium chloride solution, respectively, and then dried over sodium sulfate. After removing ethyl acetate by distillation, the residue was recrystallized from an ethyl acetate petroleum ether solvent to obtain the corresponding N-acyl amine or N-acyl hydrazine. Table 2 shows the results obtained.

FIG. 8 – FIG. 13 show the infrared spectra of N-t-butylacetamide (No. 2), N-acetyl-β-naphthylamine (No. 4), N-N-diethyl-acetamide (No. 5), N-acetyl-piperidine (No. 6), N-allyl-sinnamic acid amide (No. 7) and N-benzoyl-t-butylamine (No. 9), respectively.

Figure 8:
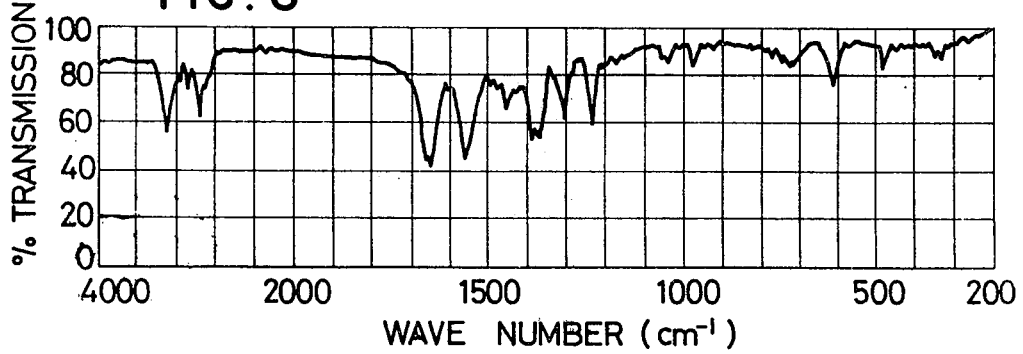

FIG. 8 shows the presence of —NH— (3310 cm$^{-1}$) and

in the amide bond (1642 cm$^{-1}$).

Figure 9:
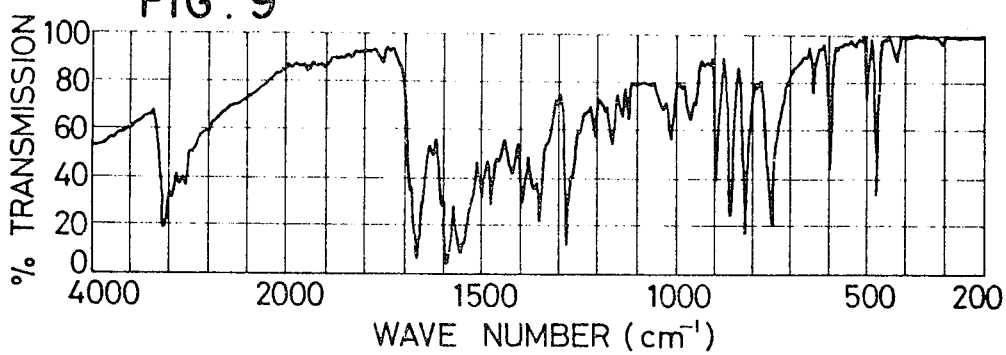

FIG. 9 shows the presence of —NH— (3270 cm$^{-1}$) and

in the amide bond (1664 cm$^{-1}$).

Figure 10:
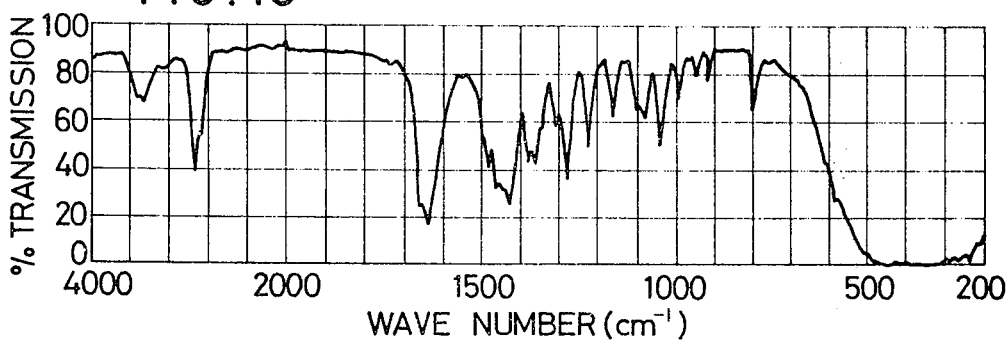

FIG. 10 shows the presence of

in the

(1632 cm$^{-1}$).

Figure 11:
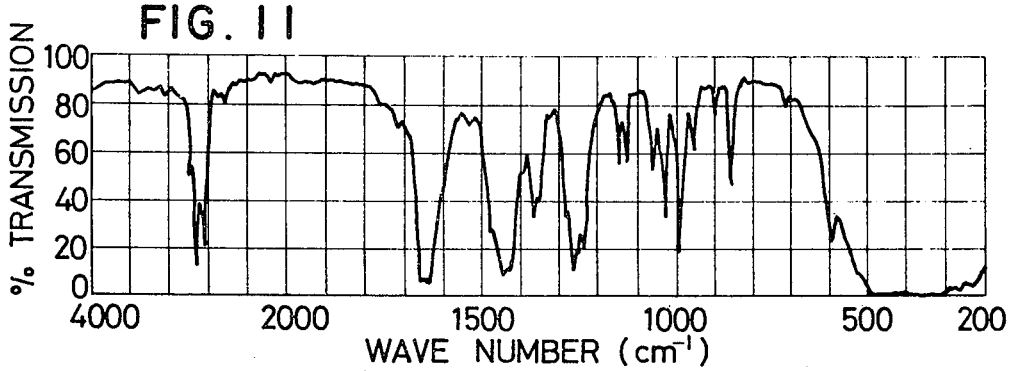

FIG. 11 shows the presence of

in the

(1638 cm$^{-1}$).

Figure 12:
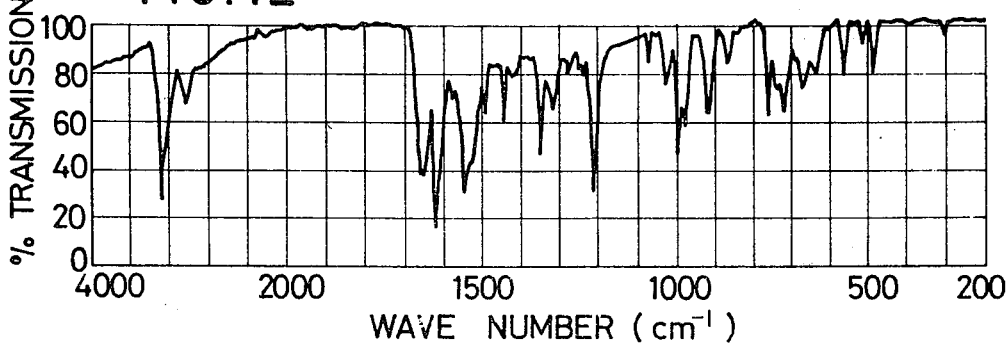

FIG. 12 shows the presence of —NH— (3300 cm$^{-1}$) and

in the amide bond (1655 cm$^{-1}$).

Figure 13:
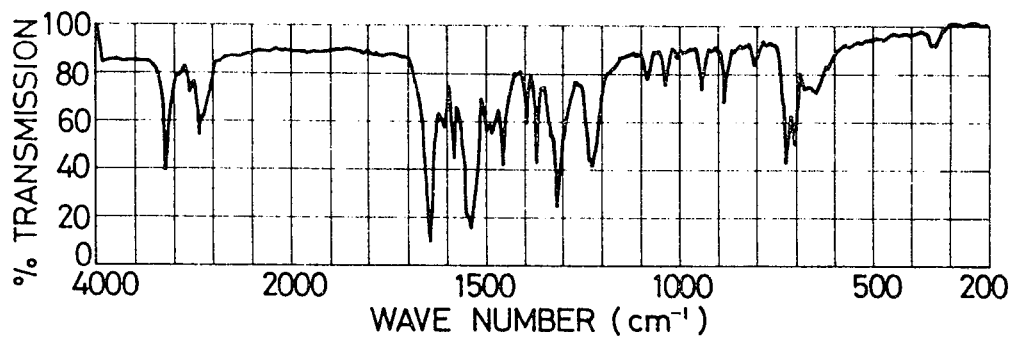

FIG. 13 shows the presence of —NH— (3310 cm$^{-1}$) and

in the amide bond (1632 cm$^{-1}$).

Table 2

| Run No. | Pyrimidine derivative | Amine or hydrazine | N-acylamine or N-acylhydrazine | Yield (%) |
|---|---|---|---|---|
| 1 | [pyrimidine]–S–C(O)–CH$_3$ | p-Toluidine | CH$_3$–C$_6$H$_4$–NH–C(O)–CH$_3$ | 98.5 |
| 2 | " | t-Butylamine | (CH$_3$)$_3$C–NH–C(O)–CH$_3$ | 98.5 |
| 3 | " | Phenylhydrazine | C$_6$H$_5$–NH.NH–C(O)–CH$_3$ | 95.6 |
| 4 | " | β-Naphthyl-amine | naphthyl–NH–C(O)–CH$_3$ | 93.9 |
| 5 | " | Diethylamine | (C$_2$H$_5$)$_2$–N–C(O)–CH$_3$ | 98.1 |
| 6 | [pyrimidine]–S–C(O)–CH$_3$ | Piperidine | piperidinyl–N–C(O)–CH$_3$ | 95.8 |
| 7 | [pyrimidine]–S–C(O)–CH=CH–C$_6$H$_5$ | Allylamine | CH$_2$=CH–CH$_2$–NH–C(O)–CH=CH–C$_6$H$_5$ | 91.0 |

Table 2-continued

| Run No. | Pyrimidine derivative | Amine or hydrazine | N-acylamine or N-acylhydrazine | Yield (%) |
|---|---|---|---|---|
| 8 | pyrimidine-2-yl S-C(=O)-phenyl | p-Toluidine | $CH_3$-C$_6$H$_4$-NH-C(=O)-phenyl | 85 |
| 9 | " | t-Butylamine | $(CH_3)_3$C-NH-C(=O)-phenyl | 96 |
| 10 | " | Phenyl-hydrazine | phenyl-NH·NH-C(=O)-phenyl | 98 |
| 11 | " | DL-Alanine ethyl ester | DL-$H_5C_2$OOC-CH(CH$_3$)-NH-C(=O)-phenyl | 98 |

| Run No. | M.P. (°C) | B.P. (°C) | Elementary analysis (%) | | | |
|---|---|---|---|---|---|---|
| | | | | C | H | N |
| 1 | 151 – 151.5 | — | Calcd. | 72.46 | 7.43 | 9.39 |
| | | | Found | 72.60 | 7.50 | 9.30 |
| 2 | 97 – 97.5 | — | Calcd. | 62.57 | 11.37 | 12.16 |
| | | | Found | 62.64 | 11.41 | 12.10 |
| 3 | 128 – 130 | — | Calcd. | 63.98 | 6.71 | 18.65 |
| | | | Found | 63.82 | 6.64 | 18.77 |
| 4 | 134 – 136 | — | Calcd. | 77.81 | 5.98 | 7.56 |
| | | | Found | 77.80 | 5.90 | 7.63 |
| 5 | — | 185 – 186 | Calcd. | 62.57 | 11.37 | 12.16 |
| | | | Found | 62.58 | 11.45 | 12.18 |
| 6 | — | 226 – 227 | Calcd. | 66.10 | 10.30 | 12.57 |
| | | | Found | 66.34 | 10.30 | 12.81 |
| 7 | 92 | — | Calcd. | 76.98 | 7.00 | 7.48 |
| | | | Found | 77.01 | 7.08 | 7.30 |
| 8 | 158 – 159 | — | Calcd. | 79.59 | 6.20 | 6.63 |
| | | | Found | 79.65 | 6.27 | 6.55 |
| 9 | 135 | — | Calcd. | 74.54 | 8.53 | 7.90 |
| | | | Found | 74.62 | 8.59 | 8.05 |
| 10 | 168 – 169 | — | Calcd. | 73.56 | 5.70 | 13.20 |
| | | | Found | 73.63 | 5.80 | 13.17 |
| 11 | 72.5 – 73 | — | Calcd. | 65.14 | 6.83 | 6.33 |
| | | | Found | 65.36 | 6.87 | 6.28 |

EXAMPLE 11

Acetyl pyrimidine-2-yl thiolester (1.12 g, 0.01 mole) obtained by using the same process as described in Example 1 was dissolved in 20 ml of ethyl acetate, and 0.01 mole of the alcohol or phenol listed in Table 3 was dissolved in the resulting solution. After addition of 10 ml of ethyl acetate to the resulting mixture, the esterification was carried out under the conditions listed in Table 3. In case 0.01 mole of acetic acid or 0.01 mole of 2-hydroxypyridine was used as a catalyst, the reaction was carried out similarly. After completion of the reaction, the precipitated 2-mercapto-pyrimidine was filtered off and the filtrate was purified by the same procedure as Example 10 to obtained the corresponding ester. Table 3 shows the obtained results.

Table 3

| Run No. | Alcohol or phenol | Ester | Yield (%) Reaction conditions | | | CH₃COOH | OH-pyridine |
|---|---|---|---|---|---|---|---|
| | | | 20 – 25°C 48 hrs. | 45 – 50°C 12 hrs. | 100 – 103°C 12 hrs. | 20 – 25°C 24 hrs. | 20 – 25°C 24 hrs. |
| 1 | β-Naphthol | naphthyl-O-C(=O)-CH₃ | 27.1 | 23.7 | 22.9 | 45.5 | 59.2 |
| 2 | Phenol | phenyl-O-C(=O)-CH₃ | 23.4 | 20.3 | 33.6 | 47.9 | 56.8 |
| 3 | Benzyl alcohol | phenyl-CH₂-O-C(=O)-CH₃ | 55.2 | 63.6 | 72.8 | 56.8 | 72.3 |
| 4 | n-Butyl alcohol | CH₃(CH₂)₂CH₂-O-C(=O)-CH₃ | 50.0 | 60.4 | 79.2 | 55.9 | 75.6 |

| M.P. (°C) | B.P. (°C) | Elementary analysis (%) | | |
|---|---|---|---|---|
| | | | C | H |
| 69 – 70 | — | Calcd. | 77.40 | 5.41 |
| | | Found | 77.50 | 5.60 |
| — | 195 | Calcd. | 70.57 | 5.92 |
| | | Found | 70.49 | 5.89 |
| — | 110 – 111 (25 mmHg) | Calcd. | 71.98 | 6.71 |
| | | Found | 71.88 | 6.79 |
| — | 125 | Calcd. | 62.04 | 10.41 |
| | | Found | 62.08 | 10.60 |

EXAMPLE 12

Acetyl pyrimidine-2-yl thiolester (0.01 mole) obtained by using the same procedure as described in Example 1 was dissolved in 20 ml of ethyl acetate, and 0.01 mole of the compound as listed in Table 4 was dissolved in the resulting solution. After addition of 10 ml of ethyl acetate to the resulting mixture, the reaction was carried out at −30°C or at 20°C for 30 minutes. After completion of the reaction, the precipitated 2-mercapto-pyrimidine was filtered off and the filtrate was washed and recrystallized by the same procedure as described in Example 10. Table 4 shows the obtained results.

compound. The infrared spectra further show that the amino or imino group is selectively acylated at −30°C because of the absence of the absorption band due to the ester bond and that both the amino or imino group and the hydroxyl group are acylated, although the latter is in a small amount, at 20°C because of the presence of the absorption band near 1710 cm$^{-1}$ due to the ester bond.

EXAMPLE 13

Benzoyl 4,6-dimethyl-pyrimidine-2-yl thiolester (2.44 g. 0.01 mole) obtained by the process of Example 4 was reacted with the amine as listed in Table 5 in ethyl acetate using a similar process to Example 10 to Table 4

| Run No. | Starting compound | Acetylated compound | Yield (%) | |
|---|---|---|---|---|
| | | | −30°C | 20°C |
| 1 | HOCH₂CH₂NH₂ | HOCH₂CH₂NH-C(=O)-CH₃ | 100 | 98.0 |
| 2 | HOCH₂CH₂NHC₂H₅ | HOCH₂CH₂N(C₂H₅)-C(=O)-CH₃ | 100 | 99.3 |
| 3 | HO-C₆H₄-NH₂ | HO-C₆H₄-NH-C(=O)-CH₃ | 96.5 | — |

Figure 14:
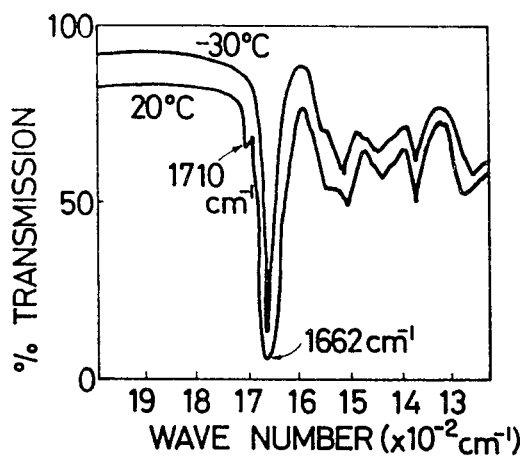
Figure 15:
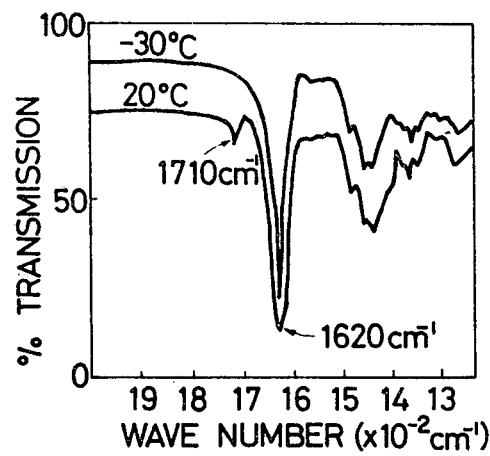

FIG. 14 and FIG. 15 show the infrared spectra of acetylated β-hydroxyethylamine (Run No. 1) and acetylated N-ethyl-β-hydroxyethylamine (Run No. 2). In the drawings, the presence of the absorption due to the C=O stretching vibration was shown at 1662 cm$^{-1}$ in the former compound and at 1620 cm$^{-1}$ in the latter yield the benzoylated product. After completion of the reaction, the precipitated 2-mercapto-4,6-dimethyl-pyrimidine was filtered off and the filtrate was washed and recrystallized using the same procedure as described in Example 10. Table 5 shows the obtained results. In Table 5, Run Nos. 5 and 6 were benzoylated at −20°C.

Figure 16:
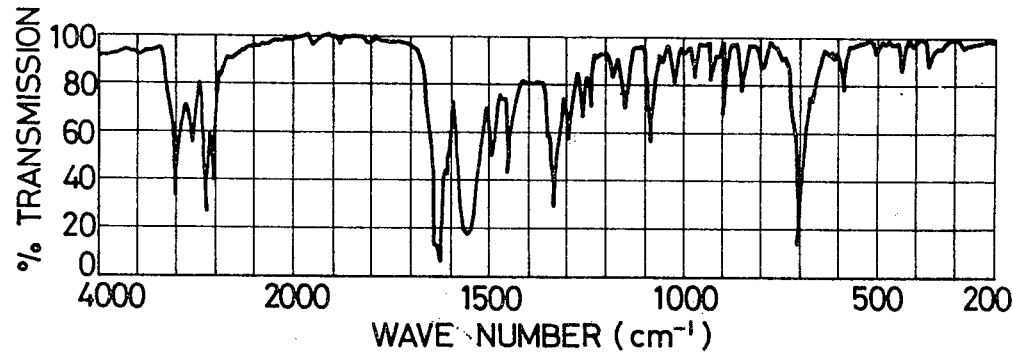

FIG. 16 shows the infrared spectrum of N-benzoyl aniline (Run No. 3). The infrared spectrum shows the presence of —NH— (3210 cm$^{-1}$) and

in the amide bond (1625 cm$^{-1}$).

progress of the reaction. After reacting two hours, the precipitates were filtered off and the filtrate was washed each two times with a saturated aqueous solution of sodium bicarbonate, a 0.5 N aqueous solution of hydrochloric acid and a saturated aqueous solution of sodium chloride and dried over anhydrous sodium sulfate. After removing the ethyl acetate by distillation from the resulting solution, there were deposited crystals, which were recrystallized from an ethyl acetate-petroleum ether solvent to obtain the dipeptide of the formula, Table 5

| Run No. | Amine | N-acylamine | Yield (%) | M.P. (°C) | Elementary analysis (%) | | |
|---|---|---|---|---|---|---|---|
| | | | | | | C | H | N |
| 1 | Diethylamine | (C$_2$H$_5$)$_2$N—CO—C$_6$H$_5$ | 97 | Oily | Calcd. | 74.54 | 8.53 | 7.90 |
| | | | | | Found | 74.60 | 8.70 | 7.91 |
| 2 | t-Butylamine | (CH$_3$)$_3$C—NH—CO—C$_6$H$_5$ | 100 | 135 | Calcd. | 74.54 | 8.53 | 7.90 |
| | | | | | Found | 74.42 | 8.60 | 7.91 |
| 3 | Aniline | C$_6$H$_5$—NH—CO—C$_6$H$_5$ | 99.2 | 163.0 | Calcd. | 79.16 | 5.62 | 7.10 |
| | | | | | Found | 79.21 | 5.77 | 7.10 |
| 4 | Piperidine | (C$_5$H$_{10}$)N—CO—C$_6$H$_5$ | 99.4 | Oily | Calcd. | 76.15 | 7.95 | 7.40 |
| | | | | | Found | 76.20 | 7.98 | 7.41 |
| 5 | N-ethyl-β-hydroxyethylamine | HO—CH$_2$CH$_2$—N(C$_2$H$_5$)—CO—C$_6$H$_5$ | 97.6 | Oily | Calcd. | 68.36 | 7.82 | 7.24 |
| | | | | | Found | 68.39 | 7.89 | 7.22 |
| 6 | β-Hydroxyethylamine | HO—CH$_2$CH$_2$—NH—CO—C$_6$H$_5$ | 100 | Oily | Calcd. | 65.43 | 6.71 | 8.47 |
| | | | | | Found | 65.49 | 6.78 | 8.41 |

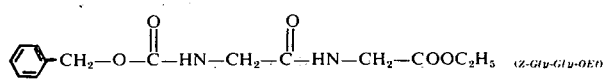

(Z-Gly-Gly-OEt)

The following Examples 14 – 19 relate to the use of the pyrimidine derivatives represented by the formula (I-a) as acylating agents in the acylation of N-terminal free amino acids or peptides, that is, the peptide syntheses.

EXAMPLE 14

2-Mercapto-pyrimidine (0.02 mole) was reacted with 0.02 mole of N-benzyloxycarbonyl-glycine using the same process as described in Example 6. The produced precipitate of dicyclohexylurea was filtered off and the filtrate was divided into two portions.

One of them was purified using the same procedure as described in Example 6 to obtain N-benzyloxycarbonyl-glycine pyrimidine-2-yl thiolester, the same compound as obtained in Example 6, in yield of 88 %.

The other of them was used for the peptide synthesis. Glycine ethyl ester hydrochloride (0.01 mole) and 0.01 mole of triethylamine were added to the other portion of the reaction solution and reacted at 0°C. The reaction took place soon and triethylamine hydrochloride and 2-mercapto-pyrimidine were precipitated with the wherein Et is an ethyl group; m.p. 83°C; yield, 95 %.

Elementary analysis:

| | C(%) | H(%) | N(%) |
|---|---|---|---|
| Calcd. for C$_{14}$H$_{18}$O$_5$N$_2$ | 57.14 | 6.16 | 9.52 |
| Found | 57.25 | 6.20 | 9.54 |

EXAMPLE 15

The crystals of N-benzyloxycarbonyl-glycine pyrimidine-2-yl thiolester (0.01 mole) obtained in Example 7 were dissolved in 50 ml of ethyl acetate, and 0.01 mole of glycine ethyl ester hydrochloride and 0.01 mole of triethylamine were added to the resulting solution. The reaction was carried out under the same conditions as described in Example 14. After completion of the reaction, the reaction solution was treated, washed, dried, and recrystallized using the same procedure as described in Example 14 to obtain Z-Gly-Gly-OEt in yield of 94 %.

EXAMPLE 16

To the reaction solution of N-protected amino acid pyrimidine-2-yl thiolester obtained by reacting 2-mercapto-pyrimidine with the N-protected amino acid listed in Table 6 using a similar process to Example 6, the amino acid ester hydrochloride listed in Table 6 was added and reacted for 1–3 hours using the same process as described in Example 14. The resulting reaction solution was then washed and recrystallized similarly to Example 14 to obtain the corresponding dipeptide. Table 6 shows the obtained results.

Table 6

| Run No. | N-protected amino acid | N-protected amino acid pyrimidine-2-yl thiolester | Amino acid ester (hydrochloride) | Dipeptide | Yield (%) |
|---|---|---|---|---|---|
| 1 | *1) Phth-Gly-OH |  | Gly-OEt | Phth-Gly-Gly-OEt | 92 |
| 2 | Z-DL-Ala-OH |  | " | Z-DL-Ala-Gly-OEt | 95 |
| 3 | Z-L-Ala-OH |  | Gly-OEt | Z-L-Ala-Gly-OEt | 93 |
| 4 | " | " | L-Met-OEt | Z-L-Ala-L-Met-OEt | 90 |
| 5 | " | " | L-Phe-OEt | Z-L-Ala-L-Phe-OEt | 92 |
| 6 | Phth-DL-Ala-OH |  | Gly-OEt | Phth-DL-Ala-Gly-OEt | 96 |
| 7 | Z-L-Phe-OH | 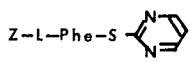 | " | Z-L-Phe-Gly-OEt | 89 |
| 8 | Z-L-Phe-OH | 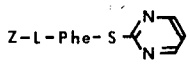 | L-Phe-OEt | Z-L-Phe-L-Phe-OEt | 97 |
| 9 | " | " | *4) L-Phe-OMe | Z-L-Phe-L-Phe-OMe | 97 |
| 10 | " | " | L-Val-OMe | Z-L-Phe-L-Val-OMe | 91 |
| 11 | Z-L-Val-OH | 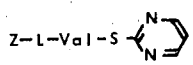 | L-Phe-OEt | Z-L-Val-L-Phe-OEt | 91 |
| 12 | " | " | L-Val-OMe | Z-L-Val-L-Val-OMe | 90 |
| 13 | " | " | L-Tyr-OMe | Z-L-Val-L-Tyr-OMe | 92 |
| 14 | " | " | Gly-OEt | Z-L-Val-Gly-OEt | 94 |
| 15 | Z-L-Leu-OH |  | Gly-OEt | Z-L-Leu-Gly-OEt | 93 |
| 16 | Z-L-Leu-OH | 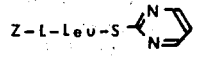 | L-Phe-OEt | Z-L-Leu-L-Phe-OEt | 96 |

| Run No. | M.P. (°C) | Specific rotation $[\alpha]_D^{20}$ | Mol. wt. | | Elementary analysis (%) | | | |
|---|---|---|---|---|---|---|---|---|
| | | | | | C | H | N | S |
| 1 | 192 | — | 290.3 | Calcd. | 57.93 | 4.86 | 9.65 | — |
| | | | | Found | 57.91 | 4.88 | 9.69 | — |
| 2 | 83 | −0.1 *2 (C=1, EtOH) | 308.4 | Calcd. | 58.43 | 6.54 | 9.09 | — |
| | | | | Found | 58.29 | 6.62 | 8.90 | — |
| 3 | 101 | −22.2 (C=1, EtOH) | 308.4 | Calcd. | 58.43 | 6.54 | 9.09 | — |
| | | | | Found | 58.28 | 6.66 | 9.02 | — |
| 4 | 79 – 80 | −23.8 (C=1, EtOH) | 368.5 | Calcd. | 55.42 | 6.57 | 7.60 | 8.70 |
| | | | | Found | 55.29 | 6.67 | 7.51 | 8.64 |
| 5 | 92 – 93 | −14.3 (C=1, EtOH) | 398.5 | Calcd. | 66.32 | 6.58 | 7.03 | — |
| | | | | Found | 66.24 | 6.61 | 6.92 | — |
| 6 | 106 | — | 304.3 | Calcd. | 59.21 | 5.30 | 9.20 | — |
| | | | | Found | 59.02 | 5.31 | 9.12 | — |
| 7 | 111 – 112 | −15.9 (C=2, EtOH) | 384.4 | Calcd. | 65.61 | 6.29 | 7.29 | — |
| | | | | Found | 65.46 | 6.46 | 7.23 | — |
| 8 | 138.5 | −18.5 *3) (C=1, D.M.F.) | 474.6 | Calcd. | 70.87 | 6.37 | 5.90 | — |

Table 6-continued

| Run No | N-protected amino acid | N-protected amino acid pyrimidine-2-yl thiolester | | | | Amino acid ester (hydrochloride) | | Dipeptide | Yield (%) |
|---|---|---|---|---|---|---|---|---|---|
| 9 | 126 - 128 | — | 460.5 | | Found Calcd. | 70.84 70.42 | 6.40 6.13 | 6.07 6.08 | — — |
| 10 | 114.5 - 115 | — | 412.5 | | Found Calcd. | 70.57 66.97 | 6.36 6.84 | 5.92 6.79 | — — |
| 11 | 139 | -27.0 (C=1, EtOH) | 426.6 | | Found Calcd. | 67.23 67.59 | 6.87 7.09 | 7.02 6.57 | — — |
| 12 | 103 - 104 | — | 364.4 | | Found Calcd. | 67.58 62.62 | 7.14 7.74 | 6.61 — | — — |
| 13 | 152 | — | 428.5 | | Found Calcd. | 62.91 64.47 | 7.75 6.59 | — 6.54 | — — |
| 14 | 166.8 | -25.9 (C=1, EtOH) | 336.4 | | Found Calcd. | 64.45 60.70 | 6.83 7.19 | 6.43 8.33 | — — |
| 15 | 102 | -24.3 (C=1, EtOH) | 350.4 | | Found Calcd. | 60.61 61.70 | 7.19 7.48 | 8.20 7.99 | — — |
| 16 | 94.5 | -21.7 (C=1, EtOH) | 440.5 | | Found Calcd. Found | 61.68 68.16 68.14 | 7.44 7.32 7.41 | 7.98 6.38 6.40 | — — — |

*1) Phth: a phthaloyl group [C₆H₄(CO—)₂]
*2) EtOH: ethyl alcohol
*3) D.M.F.: dimethylformamide
*4) Me: a methyl group

EXAMPLE 17

2-Mercapto-4,6-dimethyl-pyrimidine (0.01 mole) was suspended in 50 ml of ethyl acetate, and 0.01 mole of the N-protected amino acid listed in Table 7 was added to the resulting suspension. Further, 0.01 mole of dicyclohexylcarbodiimide was added to the resulting mixture under ice cooling and reacted for 3 hours to obtain the active ester, N-protected amino acid 4,6-dimethyl-pyrimidine-2-yl thiolester. After completion of the reaction, the produced dicyclohexylurea was filtered off and to the filtrate 0.01 mole of the amino acid or peptide ester hydrochloride listed in Table 7 and 0.01 mole of triethylamine were added and the coupling reaction was carried out at 0°C for 2 hours. After completion of the reaction, the precipitated triethylamine hydrochloride and 2-mercapto-4,6-dimethyl-pyrimidine were filtered off and the filtrate was washed, dried, and recrystallized as well as removing the solvent by distillation using the same procedure as described in Example 14 to yield the corresponding peptide. Table 7 shows the obtained results.

EXAMPLE 18

Crystals of N-benzyloxycarbonyl-L-alanine 4,6-dimethyl-pyrimidine-2-yl thiolester (0.01 mole) obtained in Example 9 was dissolved in 50 ml of ethyl acetate, and 0.01 mole of glycine ethyl ester hydrochloride and 0.01 mole of triethylamine were added to the resulting solution. The coupling reaction was carried out at 0°C for 2 hours. After completion of the reaction, the precipitate was filtered off and the filtrate was washed, dried, and recrystallized as well as removing the solvent by distillation using the same procedure as described in Example 14. The obtained crystals have a melting point of 100° – 101°C and the data of elementary analysis were agreed to those of Z-L-Ala-Gly-OEt. The yield thereof was 94 %.

Table 7

| Run | N-protected | N-protected amino acid 4,6-dimethyl-pyrimidine-2-yl thiolester | Amino acid or peptide ester (hydrochloride) | Peptide | Yield (%) | M.P. (°C) | Specific rotation $[\alpha]_D^{20}$ |
|---|---|---|---|---|---|---|---|
| 1 | Z-L-Val-OH | 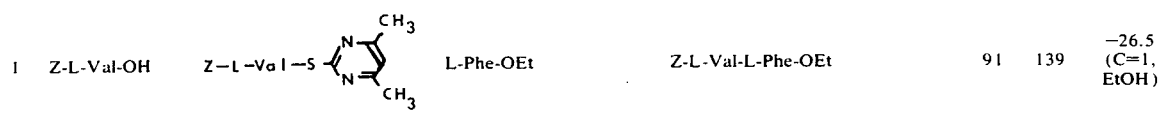 | L-Phe-OEt | Z-L-Val-L-Phe-OEt | 91 | 139 | −26.5 (C=1, EtOH) |
| 2 | Z-L-Ala-OH |  | Gly-OEt | Z-L-Ala-Gly-OEt | 95 | 100 | — |
| 3 | " | " | L-Leu-OEt | Z-L-Ala-L-Leu-OEt | 95 | 55 – 56 | −39.0 (C=1, EtOH) |

Table 7-continued

| Run | N-protected | N-protected amino acid 4,6-dimethyl-pyrimidine-2-yl thiolester | Amino acid or peptide ester (hydrochloride) | Peptide | Yield (%) | M.P. (°C) | Specific rotation $[\alpha]_D^{20}$ |
|---|---|---|---|---|---|---|---|
| 4 | Z-DL-Ala-OH | Z-DL-Ala-S-pyrimidine(CH₃)₂ | Gly-OEt | Z-DL-Ala-Gly-OEt | 95 | 82–83 | — |
| 5 | Z-L-Pro-OH | Z-L-Pro-S-pyrimidine(CH₃)₂ | L-Ala-OEt | Z-L-Pro-L-Ala-OEt | 92 | 79–80 | −74.0 (C=1, EtOH) |
| 6 | Z-L-Leu-OH | Z-L-Leu-S-pyrimidine(CH₃)₂ | Gly-OEt | Z-L-Leu-Gly-OEt | 94 | 102 | −26.3 (C=1, EtOH) |
| 7 | Z-L-Phe-OH | Z-L-Phe-S-pyrimidine(CH₃)₂ | L-Pro-Gly-OEt | Z-L-Phe-L-Pro-Gly-OEt | 85 | 93–95 | −55.0 (C=1, EtOH) |
| 8 | " | " | L-Phe-Gly-OEt | Z-L-Phe-L-Phe-Gly-OEt | 90 | 187–190 | −29.0 (C=1, EtOH) |
| 9 | Z-Gly-OH | Z-Gly-S-pyrimidine(CH₃)₂ | L-Phe-L-Ala-OMe | Z-Gly-L-Phe-L-Ala-OMe | 87 | 106–108 | −14.0 (C=1, acetone) |

EXAMPLE 19

N-benzyloxycarbonyl-glycine 4,6-dimethylpyrimidine-2-yl thiolester was synthesized using the same process as described in Example 6 except that 0.005 mole of 2-mercapto-4,6-dimethyl-pyrimidine and 15 ml of dioxane were used instead of 0.01 mole of 2-mercapto-pyrimidine and 50 ml of ethyl acetate. To the obtained reaction solution, 0.99 g (0.006 mole) of L-phenylalanine dissolved in 12 ml of a 0.5 N aqueous solution of sodium hydroxide (L-Phe-ONa) was added and reacted at 20°C for 6 hours. After completion of the reaction, the dioxane was removed by distillation. To the residue, 10 ml of water was added and the resulting solution was washed with ethyl acetate. After adjusting the solution to pH 2 with a 2 N aqueous solution of hydrochloric acid, the resulting solution was extracted with ethyl acetate. The extract was dried over magnesium sulfate and then the solvent was removed by distillation to obtain 1.44 g of Z-Gly-L-Phe-OH; yield, 80 %; m.p. 127° – 127.5°C; $[\alpha]_D = +37.0$ (C=1.0, EtOH).

What is claimed is:

1. A process for the acylation of a compound having amino and/or imino and/or hydroxyl groups, comprising reacting (1) a compound selected from the group consisting of aliphatic and alicyclic primary and secondary amines having up to about 12 carbons; nuclear unsubstituted or chlorine, nitro or methoxy nuclear substituted phenyl-$C_{1-3}$ alkyl primary or secondary amines; nuclear unsubstituted or methyl, hydroxy, carbomethyl or ethoxy nuclear substituted phenyl or naphthyl primary or secondary amines; heterocyclic primary and secondary amines of 3–6 membered rings containing one or two nitrogens and which may contain fused benzene rings; hydrazine, N-phenyl and/or N-lower alkyl-substituted hydrazines wherein at least one hydrogen of the phenyl may be substituted by nitro; amino acids of natural occurrence having free amino and/or imino groups and protected carboxyl groups; α-methylalanine; oligopeptides obtained by coupling reaction of two or more said amino acids; saccharides and steroids having amino and/or imino and/or hydroxyl groups; aliphatic alcohols having 1–12 carbons, phenol, cathechol, naphthol, benzyl alcohol and cyclohexanol, with (2) pyrimidine derivative of the formula,

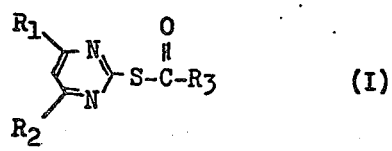

wherein $R_1$ and $R_2$ are individually a hydrogen atom or a methyl group; and $R_3$ is $C_{1-17}$ alkyl which may contain one or more halogens or hydroxyls, $C_{2-17}$ alkenyl, phenyl which may contain hydroxyl, nitro, amino, dimethylamino or methyl, naphthyl, anthryl, 5- or 6-membered hetrocyclic ring which may contain one or more hetero atoms of O, N or S, phenyl-$C_{1-5}$ alkyl which may contain methoxy, halogen, nitro or $C_{1-2}$ alkyl on the benzene nucleus, phenyl-$C_{2-5}$ alkenyl, a group of the formula

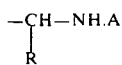

wherein R is a substituent at the α-carbon of an α-amino acid and A is hydrogen or an amine protective group for an amino acid,

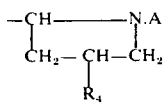

wherein $R_4$ is hydrogen or hydroxyl and A is as defined above, —$CH_2CH_2NH.A$ wherein A is as defined above,

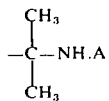

wherein A is as defined above or —$CH_2$—$(CH_2)_3$—$CH_2$—NH.A wherein A is as defined above, in an inert solvent in the presence or absence of a base at a temperature of from −50° to +100°C.

2. A process according to claim 1, wherein the compound (1) selected from the group consisting of aliphatic and alicyclic primary and secondary amines having up to about 12 carbons; nuclear unsubstituted or chlorine, nitro or methoxy nuclear substituted phenyl-$C_{1-3}$ alkyl primary or secondary amines; nuclear unsubstituted or methyl, hydroxy, carbomethyl or ethoxy nuclear substituted phenyl or naphthyl amines of 3–6 membered rings containing one or two nitrogens and which may contain fused benzene rings; hydrazine, N-phenyl- and/or N-lower alkylsubstituted hydrazines wherein at least one hydrogen of the phenyl may be substituted by nitro; saccharides and steroids having amino and/or imino and/or hydroxyl groups; aliphatic alcohols having 1-12 carbons, phenol, catechol, naphthol, benzyl alcohol and cyclohexanol is reacted with a pyrimidine derivative (2) wherein $R_3$ is $C_{1-17}$ alkyl which may contain one or more halogens or hydroxyls, $C_{2-17}$ alkenyl, phenyl which may contain hydroxyl, nitro, amino, dimethylamino or methyl, naphthyl, anthryl, 5- or 6-membered heterocyclic ring which may contain one or more hetero atoms of O, N or S, phenyl-$C_{1-5}$ alkyl which may contain methoxy, halogen, nitro or $C_{1-2}$ alkyl on the benzene nucleus, or phenyl-$C_{2-5}$ alkenyl.

3. A process according to claim 1, wherein the compound (1) selected from the group consisting of amino acids of natural occurrence having free amino and/or imino groups and protected carboxyl groups, α-methylalanine oligopeptides obtained by coupling reaction of two or more said amino acids, is reacted with a pyrimidine derivative of the formula,

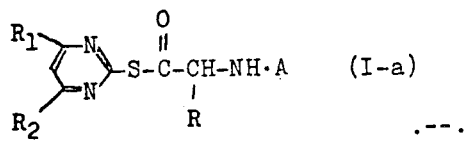

4. A method according to claim 1, wherein the inert solvent is dioxane, chloroform, methylene chloride, or ethyl acetate.

5. A method according to claim 1, wherein the base is a tertiary amine, or a hydroxide, carbonate or bicarbonate of alkali metal.

6. A method according to claim 5, wherein the tertiary amine is triethylamine, N-alkylmorpholine, N,N-dialkylaniline, pyridine or xynoline.

7. A method according to claim 5, wherein the hydroxide, carbonate or bicarbonate of alkali metal is potassium hydroxide, sodium hydroxide, potassium carbonate, sodium carbonate, potassium bicarbonate or sodium bicarbonate.

* * * * *